(12) United States Patent
Morishige

(10) Patent No.: US 6,454,695 B1
(45) Date of Patent: Sep. 24, 2002

(54) THERAPEUTIC INSTRUMENT FOR TREATING OR RELIEVING PSORIASIS, ATOPIC DERMATITIS, ARTICULAR RHEUMATISM AND/OR CANCER OR PREVENTING THE PROGRESS OF THESE DISEASES AND METHOD OF UTILIZATION THEREOF

(75) Inventor: Fukumi Morishige, Chiba (JP)

(73) Assignees: Fumie Morishige, Chiba (JP); Noritsugu Morishige, Omura (JP)

( * ) Notice: Subject to any disclaimer, the term of this patent is extended or adjusted under 35 U.S.C. 154(b) by 0 days.

(21) Appl. No.: 09/601,544

(22) PCT Filed: Feb. 3, 1999

(86) PCT No.: PCT/JP99/00446

§ 371 (c)(1),
(2), (4) Date: Aug. 3, 2000

(87) PCT Pub. No.: WO99/39771

PCT Pub. Date: Aug. 12, 1999

(30) Foreign Application Priority Data

Feb. 5, 1998 (JP) .............................. 10/39641
May 8, 1998 (JP) ............................. 10/142195

(51) Int. Cl.[7] ................................. A61N 5/00
(52) U.S. Cl. ............................................. 600/1
(58) Field of Search ........................ 600/1–8

(56) References Cited

U.S. PATENT DOCUMENTS

| | | | | | |
|---|---|---|---|---|---|
| 4,314,909 A | * | 2/1982 | Beall et al. | ..................... | 588/11 |
| 4,382,974 A | * | 5/1983 | Yannapoulos | ................... | 427/5 |
| 4,815,448 A | * | 3/1989 | Mills | .............................. | 600/2 |
| H1013 H | * | 1/1992 | Wormsbecher et al. | ........ | 588/12 |
| 5,282,781 A | * | 2/1994 | Liprie | ............................ | 600/3 |
| 5,342,283 A | * | 8/1994 | Good | .............................. | 600/8 |
| 5,433,693 A | * | 7/1995 | Ott | .................................. | 600/1 |
| 5,771,472 A | * | 6/1998 | Carpena et al. | ................. | 588/2 |
| 5,833,593 A | * | 11/1998 | Liprie | ........................... | 600/3 |
| 5,858,465 A | * | 1/1999 | Hunt et al. | ............... | 427/248.1 |
| 6,023,006 A | * | 2/2000 | Fiquet et al. | ................... | 588/2 |

FOREIGN PATENT DOCUMENTS

| | | |
|---|---|---|
| JP | 36-3385 | 2/1964 |
| JP | A 54-106091 | 8/1979 |
| JP | 60-132741 | 12/1983 |
| JP | A 61-40332 | 2/1986 |
| JP | A 62-32948 | 2/1987 |
| JP | A 64-21479 | 1/1989 |
| JP | 6-343708 | 6/1993 |
| JP | A 8-59488 | 3/1996 |

OTHER PUBLICATIONS

Irie, *Radiation Therapy Respective for Disease*, Kokuseido Shuppan K.K., pp. 61, 65, and 92, (1967).
Egawa, *Manual for Cancer Therapy by Radial Rays*, Chutai Igaku Sha K. K., pp. 11–13, (1989).
Luckeg, *Radiation Hormesis*, pp. 103 second paragraph, (1991).

\* cited by examiner

Primary Examiner—Kevin Shaver
Assistant Examiner—Joseph A. Cadugan
(74) Attorney, Agent, or Firm—Oliff & Berridge, PLC

(57) ABSTRACT

A therapeutic instrument for treating psoriasis, atopic dermatitis, articular rheumatism and/or cancer or preventing the progress thereof which includes a solid radiation source having a half-life within a range of from 20 to $1.41 \times 10^{10}$ years and a radioactivity corresponding to a decay rate within a range of from 10 to 370 Becquerel/g and a solid material coating the same, characterized in that the solid material has a radiation face for radiating radial rays emitted from the radiation source. As the radiation source, use is made of, for example, monazite, while a cotton bag, Japan wax, etc. are usable as the solid coating material.

22 Claims, No Drawings

THERAPEUTIC INSTRUMENT FOR TREATING OR RELIEVING PSORIASIS, ATOPIC DERMATITIS, ARTICULAR RHEUMATISM AND/OR CANCER OR PREVENTING THE PROGRESS OF THESE DISEASES AND METHOD OF UTILIZATION THEREOF

BACKGROUND OF THE INVENTION

1. Field of Invention

The invention of the present application relates to a therapeutic instrument for treating psoriasis, atopic dermatitis, articular rheumatism and/or cancer or preventing the progress of these diseases.

2. Description of Related Art

There has been at least carried out low dose irradiation of radial rays such as X-rays for treating psoriasis by means of radial rays (Hideo Irie, Radiation therapy respective for diseases, page 61, published by Kokuseido Shuppan K. K. (edition; Feb. 10, 1967)). However, the irradiated doses are divided into several low irradiation doses such as from 100 to 150 R (from 0.91 to 1.37 sieverts (Sv) (from 0.91 to 1.37 grays (Gy)). The total irradiation dose for several low irradiation doses becomes high such as, for example, 200 to 600 R (1.8 to 5.4 Sv (1.8 to 5.4 Gy)). Highly skilled technique is required for administering these radial rays.

For atopic dermatitis, there is no known therapy that can be carried out safely by means of low dose irradiation of radial rays.

For articular rheumatism, low dose irradiation of radial rays such as X-rays has been carried out as therapy (Hideo Irie, Radiation therapy respective for diseases, page 92, as described above). However the X-ray intensities of low dose irradiation are very high such as, for example, 80 to 100 kV for small joints and from 140 to 180 kV for large joints. Furthermore, therapy includes 5 to 10 low dose irradiations. Thus, the total irradiation dosage becomes high such as, for example, 50 to 1000 R (10 to 50 R for an acute phase, 70 to 100 R for a chronic phase) (0.46 to 9.1 Sv (0.46 to 9.1 Gy)). For therapy by means of X-ray irradiation, highly skilled technique is required as in the above-mentioned therapy for atopic dermatitis, which makes administration difficult.

For cancer therapy, X-rays are administered in a total dosage of from 3500 to 6000 rads (from 35 to 60 Sv (from 35 to 60 Gy)) (Jun Egawa, "Manual for cancer therapy by radial rays", page 12, Chugai Igaku Sha K. K. 1989). High skilled technique is also required for the therapy by X-ray irradiation as in the above-mentioned therapy for psoriasis, which makes administration difficult.

In the case of skin cancer, the irradiated doses by means of X-rays, $^{60}$Co or $^{137}$Sr etc. are very high such as 200 R (1.9 Sv) per one time for 20 times or more every day or every two days (Hideo Irie, Radiation therapy respective for diseases, page 65, as described above).

As to other methods, the following applies "Irradiation of low dose ionized rays promotes cancer growth inside of the body. In the case of a terminal phase of cancer, an increase in a growing speed is eminent. However, the greatest effect of systemic irradiation by low dose ionized rays is to activate an anti-tumor protective mechanism in the body. As the result, growth and development of cancer are suppressed to lower the mortality by cancer." ("Radioactive hormesis II" (1992, Soft Science K. K., Tokyo) (original book, T. D. LUCKEY, "RADIATION HORMESIS", CRC Press, Inc., Boca Raton, 1991), page 103, the second paragraph).

However, systemic irradiation is essential for the method, thus practical administration is quite difficult.

Thus, there is a need for a therapy, the administration of which is substantially easier and safer, a therapy that does not require a dangerous radiation source such as, for example, an X-ray irradiation device.

DESCRIPTION OF THE INVENTION

The inventor of the present application has investigated and discovered a therapy by means of very low dose radiation without systemic irradiation and invented a therapeutic instrument to be used for the therapy and a preparation method therefor. That is, the invention relates to a therapeutic instrument for treating psoriasis, atopic dermatitis, articular rheumatism and/or cancer or preventing the progress thereof which is composed of a solid radiation source having a half-life within a range of from 20 to $1.41 \times 10^{10}$ years and a radioactivity corresponding to a decay rate within a range of from 10 to 370 Becquerel/g with a solid material coating the same, characterized in that the above-mentioned solid material has a radiation face for radiating radial rays emitted from the said radiation source.

Psoriasis, atopic dermatitis, articular rheumatism and cancer to be targeted by the therapy include not only in human beings but also in general mammals such as domestic animals and pet animals.

From the therapeutic instrument according to the invention, very low dose radial rays are irradiated which are within an amount that is practically harmless to the human body even though radiation is continued on the human body for long periods such as, for example, several years.

The radioactivity range of the radiation source used in the invention of the application is within a limit of radioactivity concentration for nucleic materials of such a low level that any report to the Science and Technology Agency in Japan is not necessary. That is, it is within the limit corresponding to a decay rate range of 370 Becquerel/g or less. For respective radioactivity radiated from the solid radiation source, it means that radioactivity corresponds to the decay rate within a range of from 10 to 370 Becquerel/g, preferably from 100 to 370 Becquerel/g, more preferably from 200 to 370 Becquerel/g, and most preferably from 300 to 370 Becquerel/g, or furthermore preferably from 100 to 200 Becquerel/g, 100 to 320 Becquerel/g, 200 to 320 Becquerel/g or 150 to 270 Becquerel/g. If the human body is practically undamaged by irradiation for the long period, the total dose of various radial rays may exceed 370 Becquerel/g.

The radiation source is a radioactive element of $^{40}$K, $^{87}$Rb, $^{113}$Cd, $^{116}$In, $^{123}$Te, $^{138}$La, $^{144}$Nd, $^{147}$Sm, $^{148}$Sm, $^{152}$Gd, $^{176}$Lu, $^{174}$Hf, $^{187}$Re, $^{188}$Os, $^{190}$Pt, $^{227}$Th, $^{232}$Th, $^{235}$U, $^{237}$Np or $^{238}$U or a radioactive decay series in which $^{232}$Th, $^{235}$U, $^{237}$Np or $^{238}$U is a parent.

Preferably, the radiation source is a radioactive element of $^{232}$Th, $^{235}$U, $^{237}$Np or $^{238}$U or a radioactive decay series in which any of the elements is a parent.

More preferably, the radiation source is a radioactive element of $^{232}$Th or $^{235}$U or a radioactive decay series in which any of the elements is a parent.

Still more preferably, the radiation source is a radioactive element of $^{232}$Th or a radioactive decay series in which the element is a parent.

The radiation source can maintain quite low dose radioactivity stably for the long period, wherein a half-life is within a range of from 20 to $1.41 \times 10^{10}$ years.

It is preferable that the radiation source is a natural ore, preferably a natural ore containing a radioactive element of $^{232}$Th, $^{235}$U, $^{237}$Np or $^{238}$U or a radioactive decay series in which any of the elements is parent, more preferably a radioactive element of $^{232}$Th or $^{238}$U or a radioactive decay series in which any of the elements is parent, and more preferably a radioactive element of $^{232}$Th or a radioactive decay series in which the element is parent.

Preferably, the radiation source is monazite containing from 3 to 15% (calculated as $^{232}$ThO$_2$) of a radioactive decay series in which $^{232}$Th is parent.

The solid material used in the therapeutic instrument according to the invention may be any solid material which can prevent scattering of the radiation source by coating the radiation source with the solid material and which can radiate γ-ray with or without β-ray from the surface of the solid material in the therapeutic instrument according to the invention.

Methods of coating the radiation source with the solid material include coating the radiation source, which is generally in the form of gravel, granules or preferably powders, by placing them in a flexible or solid vessel such as a bag, a can and a box, and a method to coat the radiation source bodies or particles or body groups or particle groups in the form of gravel, granules or preferably powders with molten solid material individually and cooling them.

When using a bag to coat the radiation source, the bag is, if desired, quilted by connecting the parts of the upper and lower faces with threads or strings to assure that powders of the solid radiation source are distributed evenly. The bag becomes an approximate plate form with a thickness of from 5 to 20 mm excepting quilted parts when filled with the powders of the solid radiation source.

The vessel such as a bag, a can and a box composed of solid material for receiving and coating the radiation source is made of a material that does not irritate the skin, such as, for example, mineral ores and metal compounds such as metal oxides, for example glass or fibers thereof; metals or metal fibers: synthetic organic materials such as plastics or fibers thereof; cotton, silk, paper, wool, leather, natural rubber and/or synthetic rubber. The form thereof is a soft and flexible textile, nonwoven fabric, membrane or plate. The membrane and the plate may be porous.

Examples of plastics that may be used include: polyalkylene plastics such as polyethylene, polypropylene, polybutylene, polyisobutylene and polyacryls; natural rubber; polyester type plastics such as PET; silicone resins; and polyamide resins such as nylon. It is possible to use reinforced plastics in order that the vessel is not destroyed easily by cutting, abrasion or tearing.

Furthermore, the solid material may be, if desired, quilted or sectioned in order for powders of the solid radiation source to be evenly distributed. The vessel becomes an approximate plate form with a thickness of from 5 to 20 mm except for quilted parts or sectioned parts when filled with the powders of the solid radiation source. The solid material may be a soft and flexible textile, membrane or plate made of metal.

Metal, as the solid material, is preferably in the form of a plate having a thickness of from 0.1 to 3 mm. It is preferably an anti-corrosive metal plate, a metallic plate with a preserved surface or a stainless steel plate.

Preferably, the metallic plate is an anodized aluminum plate, a tin plate, a zinc-plated iron plate, an enamel plate, a plastic-coated iron plate, a stainless steel plate or a lead plate.

Preferably, the solid material is a soft and flexible textile, nonwoven fabric or membrane made of cotton, silk, paper, wool, leather, natural rubber and/or synthetic rubber.

Thus, by coating the radiation source with the solid material, scattering of the radiation source can be prevented and γ-ray with or without β-ray can be radiated from the surface of the solid material.

The thickness of the coating parts in the vessel is generally from about 0.1 to 3 mm. The thickness may be deviated from that range according to the desired strength (abrasion resistance, cutting resistance, tear resistance). And, any thickness may be used if the major part of γ-ray can be transmitted therethrough.

A whole or a part of the outer surface of the solid material which coats the radiation source may also be coated with other material for filtering a part of γ-ray, except for the radiation face which radiates radial rays of mainly γ-ray toward skins to be irradiated.

The radiation face for radiating radial rays includes a part or, for rare cases, a whole of the surface of the solid material which is coated with the radiation source. It is preferably a surface of an easily deformable flexible solid body such as a bag in order to arrange the surface to fit it on the skin surface.

The distance between the radiation face for radiating very low dose radial rays and the irradiated part affected with the above-mentioned diseases such as psoriasis may be any one provided that the radial rays can be utilized practically and efficiently. Generally, the radiation face for radiating radial rays may be separated from the affected skin surface for a distance of from 0 to 50 mm in a direction perpendicular to the skin surface.

If necessary, direct contact between the radiation face of the instrument and the skin may be avoided by positioning a sheet or fabric (which may be hygroscopic for absorption of sweat) made of a radioactively transparent material which seldom absorbs γ-rays between the radiation face of the instrument and the skin.

The shape of the radiation face may be a flat face, a bent face or a corrugated face or mixture thereof. It may be preferably any one among the above-mentioned shapes provided that very low dose radial rays can be utilized efficiently and that it can minimize radiation on unaffected parts.

The radiation face may be continuous or discontinuous.

In the case of continuous radiation face, it may be one piece of a flat face, a corrugated face such as a washing plate face, a face consisting of multiple bent faces or a roughened face. It may also be a surface of a bag made of textile, nonwoven fabric or fabric.

If the radiation face of the solid material is a discontinuous flat face, multiple radiation faces are connected by joints in order to make the multiple flat radiation faces fitted with the surface form of the skin on which the instrument is worn. For example, the face may be bent freely according to the surface form of the affected skin part on which the instrument is worn. The joints used in that case may be strings, chains, fabrics, textile or wires to be connected with respective flat constitutional parts.

In order to collect natural ores containing the radiation source such as mineral radioactive isotopes near the radiation face which radiates radial rays, the following method may be carried out. That is, the solid material is molten, and powders of the above-mentioned natural ore are blended into the molten material. The blend is allowed to leave as such with maintaining the temperature in the vessel having the flat bottom inner face, during which the powders are deposited by utilizing the gravity difference between of the solid material and the powders. Thereby, powders of the mineral ore are collected at the bottom of the vessel. After collection, the molten material is cooled to solidify and removed from the vessel. The part contacted with the inner bottom face of the vessel is used as the radiation face of the therapeutic instrument according to the invention.

To this end, it is necessary that the solid material is solid at the normal temperature and that the material has enough low viscosity to deposit particles and/or powders of the natural ore containing natural radioactive isotopes and lower specific gravity than that of the above-mentioned natural ore.

Examples of preferable solid materials having such properties include: inorganic oxides having lower specific gravities than natural ores such as glass, Pyrex, or silicon oxides such as crystals, ester type and/or paraffin type waxes.

Ester type waxes include plant waxes such as Caunauba wax, Japan wax and sugar wax, as well as animal waxes such as beeswax, insect wax, whale wax and wool wax.

Hydrocarbon waxes may include paraffin waxes and microcrystalline waxes. Additionally, synthetic waxes may include carbon wax and polyethylene wax.

It is essential that these waxes effect no reactions such as, for example, skin burns, allergies, eruptions or absorptions when in contact with the skin of human beings or mammal.

Preferable waxes may include Japan wax and beeswax.

The invention of the present application also relates to a method for preparing the above-mentioned therapeutic instrument or a part thereof, that is, a method for preparing a therapeutic instrument for treating or relieving psoriasis, atopic dermatitis, articular rheumatism and/or cancer or preventing the progress of these diseases by mixing a natural ore containing natural radioactive isotopes with molten ester type and/or paraffin type wax uniformly, then introducing the obtained mixture in a casting type mold to deposit the natural ore at the bottom of the mold while maintaining the wax in the molten state, and then solidifying the ore in deposited state.

Part of the therapeutic instrument obtained by the above-mentioned preparation method may be in the form of a flat plate or a bent plate formed into a triangle, square, rectangle, right hexagon, circle, oval or polygon with or without irregularity.

The therapeutic instrument according to the invention can be prepared by connecting multiple parts of the therapeutic instrument with each other in such a way as to form either a flat face or a bent face, by which the skin to be fitted with the therapeutic instrument, according to the invention, can be covered with these multiple radiation faces.

As described above, irradiation energy of radial rays radiated from the prepared therapeutic instrument according to the invention is quite low.

For the case of a cotton bag in which powders (from 30 to 50 mesh) of monazite having a value of 220 Bq/g supposed from γ-ray determination and 350 Bq/g supposed from β-ray determination, the dose of irradiated radial rays is 20 $\mu$Sv/lr in the central surface part of the bag for the thickness of about 30 mm and the monazite amount of 700 g. The therapeutic instrument having such thickness is used mostly for skin diseases such as psoriasis, atopic dermatitis and skin cancer.

The dose of irradiated radial rays is 50 $\mu$Sv/hr in the central surface part of the bag for the case in which thickness of monazite powders (from 30 to 50 mesh) is about 50 mm and the monazite amount is 5 kg. The therapeutic instrument having such thickness is used mostly for treating affected parts deep inside the body (e.g., articular rheumatism, respiratory cancer and digestive cancer) or preventing the recurrence thereof.

Irradiation energy varies depending on the radiation source used as well as the thickness and the width of the radiation source. For example, when the therapeutic instrument is a bag containing the radiation source, it is relatively low at ends of the radiation face and relatively high at the central part of the radiation face, and there is a tendency of increase in the irradiation energy at the central part with increase in the thickness of the bag or the area of the radiation face.

For the case of using the above-mentioned powders of monazite in a cotton bag (the case in which the solid material is a cotton fabric), the thickness may be within the range of from about 5 mm to 100 mm, preferably from 5 to 50 mm. Irradiation energy at the central part of the radiation face is within the range of generally from 10 to 100 $\mu$Sv/hr, preferably from 30 to 50 $\mu$Sv/hr. However, the range of irradiation energy may be deviated from the indicated range to a higher one depending on a continuous or discontinuous irradiation period provided that it is within a range harmless to the human body practically.

When treating cancer which is a disease occurring inside of the body or preventing the progress thereof, the therapeutic instrument according to the invention may be embedded in a part of the body that is nearest to the affected part.

For such case, the solid radiation source should be coated with the solid material or evenly dispersed in the solid material. The form thereof may be of any type.

The solid radiation source coated with the solid material may be positioned in multiple forms such as, for example, a particulate one at the site to be treated or relieved.

The therapeutic instrument according to the invention may be arranged in the part that is nearest to the affected site, such as, for example, outside or inside of a tubular cavity such as the oral cavity, the gullet and the intestine, the inside of the vagina or the outside of a blood vessel, the breast cavity and the abdominal cavity, instead of the above-mentioned embedding.

The solid material to be embedded is a non-toxic material that is not easily influenced by endometabolism such as silicone resins or high molecular chemical materials. Furthermore, it is possible to fix the radiation source in artificial blood vessels (grafts) prepared from these materials.

Progress of the therapy is judged by observation of skin surface for the cases of psoriasis and atopic dermatitis.

Within the period for irradiating very low dose radial rays from the radiation face of the therapeutic instrument according to the invention, the condition of psoriasis or atopic dermatitis gradually disappears.

The period for positioning the radiation face of the therapeutic instrument on the entire surface of the affected skin or a part thereof may be continuous or discontinuous.

Generally, the radiation face of the therapeutic instrument is positioned on the surface of the affected skin for from 6 to 16 hours per day.

Generally, days required for recovery of psoriasis or atopic dermatitis are about 3 months for the case that the therapeutic instrument is positioned on the surface of the affected skin for from 6 to 16 hours per day. However, the period varies depending on the condition of psoriasis or atopic dermatitis.

The irradiated dose by the therapeutic instrument according to the invention for such a case is 20 ($\mu$Sv/hr)×16 hr×365 day=116,800 $\mu$Sv/hr=about 120 millisievert/y, calculated from treatments of 16 hours per day for 1 year. The irradiated dose is quite low compared with the irradiated dose of X-rays for the conventional therapeutic case of psoriasis, that is from 1.8 to 5.4 Sv. The low dose can also apply for skin cancer.

When the shape of the affected skin is not flat, parts of a therapeutic instrument having a flat or bent radiation face as described above are connected with joints, if necessary, to form the radiation face suitably, i.e., according to the shape of the skin surface. It can be then positioned on the surface of the part affected with psoriasis for treating. Furthermore, the radiation face of the soft and flexible bag can be positioned on the surface of the part affected with psoriasis or atopic dermatitis.

Therefore, the invention of the present application relates also to a method for treating or relieving psoriasis or atopic dermatitis by radioactively applying the radiation face of very low dose according to the invention on a part or a whole of the skin affected with psoriasis or atopic dermatitis by means of radial rays.

From the results for the therapeutic instrument used until now, there are found some cases in which light recurrence of psoriasis or dermatitis after a certain period even after an apparent full recovery. For such cases, it is preferable to irradiate by means of the therapeutic instrument for psoriasis according to the invention for from 1 hour to 16 hours, preferably from about 1 hour or 6 hours to 16 hours, only while the patient is asleep and to monitor the symptoms due to psoriasis or atopic dermatitis periodically for the residual life of the patient.

Since the irradiated dose by means of the therapeutic instrument for psoriasis according to the invention is within a very low range that is substantially harmless to the human body, there is supposedly no disorder caused by irradiation of radial rays with the therapeutic instrument according to the invention. Even for the cases wherein a very light damage such as a partial defect on gene sequence occurs, irradiation is discontinuously applied and there is a non-irradiated period of several hours, during which the defect in the gene sequence can be recovered enough. Therefore, even if the therapeutic instrument according to the invention is used for a long period, it is not expected to cause gene disorder such as skin disease and marrow functional disorder. Practically, no condition corresponding to such gene disorders has been observed by the inventor.

For the therapy of psoriasis and atopic dermatitis by means of the therapeutic instrument according to the invention, it is considered in one aspect that very low dose radial rays radiated from the radiation face of the above-mentioned therapeutic instrument can expel cells (lymphocytes) relating to the immune system and the allergy system collected on the above-mentioned affected skin, thereby the above-mentioned diseases are eliminated.

For treating the skin diseases sited topically such as psoriasis and atopic dermatitis by means of the therapeutic instrument according to the invention, an amount of the radiation source can be decreased less than that for the cases of treating diseases at deep parts such as articular rheumatism and cancer per an unit area of skins on which the therapeutic instrument is fitted, for example half the amount.

For preventing the progress of articular rheumatism and cancers, for instance cancers in the liver, the spleen, the peritoneum, the mediastinum organ, the lung, the pleura and the thorax present in a deep part of the body or relieving or treating these diseases, similarly to the skin diseases such as psoriasis and atopic dermatitis, the therapeutic instrument according to the invention may be fitted on or near the skin surface nearest to the affected parts. For such cases, it is not systemically fitted and at most only an amount enough to cover the affected parts is used. Since the affected parts are deep inside the body and somewhat removed from the radiation source, from 1 to 3 times the radiation source for the case of treating skin diseases, and optionally 5 times of the radiation source may be used.

The fitting period of the therapeutic instrument according to the invention for targeting articular rheumatism or cancer is from 8 hours to 24 hours every day.

If 100 ($\mu$Sv/hr), which dose is 5 times of the case for skin diseases, is irradiated every day for 24 hours, the total dose for 1 year becomes $$100(\mu Sv/hr) \times 24\ hr \times 365\ day\ 0.876(Sv).$$

The irradiated dose is quite low compared with the conventional X-ray irradiated dose for the case of chronic articular rheumatism which is at least 3.15 Sv (3.15 Gy). Similarly, it is a very low dose compared with the irradiated dose for relieving or treating cancer present deeply inside of the body, which is at least from 30 to 60 Sv (from 30 to 60 Gy). And, the irradiating period by means of the therapeutic instrument according to the invention is long such as 1 year, but it is different from the irradiation period for X-ray divided irradiation. Thus, irradiation energy per unit time is quite low.

Additionally, any erythema is not recognized by the therapeutic instrument according to the invention after 2 years irradiation.

The invention of the present application is illustrated in more detail by the following Therapeutic Examples. The invention of the present application is not limited by these Examples and Therapeutic Examples.

Test Example: As the radiation source used in the following Examples and Therapeutic Examples, monazite produced in Kwangtung, China (composed of phosphates of Ce, La, Y and Th; about 5% of Th is contained as $ThO_2$) was used.

Data relating to radial rays of the monazite is as follows.
1. Determination by means of a survey meter (sample amount; 5 g)
   (1) Scintillation survey meter (Aloka TCS-161) 0.6 $\mu$Sv/hr (BG: 0.07 $\mu$Sv/hr)
   (2) GM survey meter (Aloka TCS-11) 3 $\mu$Sv/hr (BG: 0.3 $\mu$Sv/hr)
2. Determination of energy spectrum
   (1) Gamma counter (sample amount; 5 g) (LKB 1282 COMPUGAMMA)
      (a) agreed with energy spectrum of $^{232}$Th
      (b) radioactive dose (47 keV to 1436 keV) when $^{232}$ThO$_2$ was used as a standard ray source sample 11649 cpm/5 g (sample) $^{232}$ThO$_2$ 362204 cpm/0.88 g ($^{232}$Th) 1 g of the sample is 220 Bq, since 1 g of $^{232}$Th is 4070 Bq.
   (2) Liquid scintillation counter (sample 1 g) (Packard 2250CA) 21074 dpm (BG: 60 dpm) 350 Bq/(sample) 1 g

EXAMPLE 1

Powdery monazite described above of about 30 to 50 mesh which was not fine enough to pass the weaves was added in a quilted bag made of cotton fabric, to make the bag as a plate form having the thickness of about 15 mm to 50 mm except for quilted parts.

For the case in which the thickness of monazite was about 3 cm and the amount of monazite was 700 g (width; about 5 cm, length; about 10 cm), the radiation dose on the surface of central part of the bag radiation face was 20 $\mu$Sv/hr. This therapeutic instrument is mostly used for treating psoriasis and atopic dermatitis.

For the case in which the thickness of monazite was about 5 cm and the amount of monazite was 5000 g (width; about 15 cm, length; about 30 cm), the radiation dose on the surface of central part of the bag radiation face was 50 $\mu$Sv/hr. This therapeutic instrument is mostly used for relieving affected sites or preventing the recurrence thereof (articular rheumatism, lung cancer and digestive cancers) at deep parts in the body.

EXAMPLE 2

Into a fabricated wood frame having the inner depth of 1.5 cm, the inner width of 5 cm and the inner length of 10 cm, a cotton connecting string was introduced if necessary by contacting with the inner side and/or if necessary by contacting a cotton fabric for protection of Japan wax to be formed later by coagulation with the inner side of the vessel. Then, 100 g of the above-mentioned monazite which had been pulverized to about from 30 to 200 mesh was introduced in molten Japan wax corresponding to about 45 ml when molten, and stirred enough, and then the suspension of monazite was injected in the above-mentioned frame. Then, the temperature was maintained at about 60 to 70° C. for 1 hour to deposit powders of monazite at the bottom of the wood frame, and thereafter allowed to cool and coagulate. Then the Japan wax plate formed by coagulation was removed from the wood frame, or removed from the wood frame in together with the above-mentioned cotton fabric. The laminar Japan wax plate was used as a therapeutic instrument for psoriasis, alone or in conjunction, for several necessary times via connecting strings each other. The therapeutic instrument for psoriasis was used in such a way to contact with or arrange near a part or a whole of the part affected with psoriasis.

Therapeutic Example 1 (Psoriasis Therapeutic Example 1)

The patient was 51-year-old male (occupation; company employee). Several years ago, papules with itch were formed on the stretching site of the right antebrachium and the number thereof increased gradually. Papules fused gradually and scales accompanied. Although he was examined by the neighbor doctor, lesions on skin were enlarged increasingly to extend over the branchia and the antebranchia is both the membra, and light red papules accompanied with scales were observed at expansible and contractible parts of the membra inferius. From 1 year ago, lesions on the skin were expanded over a wide range to the back of the body accompanied with vigorous itches. Although he was treated by several dermatologists, there was not attained any effect.

When he was examined in the inventor's clinic for the first time, he complained of insomnia due to the itches, and his clothes had an odor of dropped scales. His disease was diagnosed as conventionally observable common psoriasis.

A therapeutic instrument according to the invention of the application similar to that prepared in the above-mentioned Example 1 in a form of a quilted bag (the thickness of about 10 mm, 170 cm×60 cm) containing pulverized monazite (from 60 to 70 mesh) was fitted, only while sleeping, near to whole parts affected with psoriasis at the limbs and the back of the body for irradiation, and was observed. Itches were relieved after 1 week. After 1 month, scales and papules disappeared and only light pigmentation remained on traces of papules. After another 3 months, pigmentation became inconspicuous.

Thereafter, the patient discontinued fitting and irradiation while sleeping because of being relieved. 1 Month after commence of discontinuance, 3 or 4 small red points of little finger size in treetop form appeared at the stretching site of the right antebrachium, the incipient site. Itches accompanied the appearance of the red points. By fitting the instrument again, similar to the above-mentioned way, only while sleeping, lesions on the skin disappeared within a short period of time.

During the above-mentioned therapy, there was no apparent condition corresponding to radial ray disorders such as sore skin at the fitted site of the therapeutic instrument for psoriasis according to the invention, weary fatigue and/or decrease in leucocytes.

As described above, by fitting (that is, irradiating low dose radial rays) the therapeutic instrument for psoriasis according to the invention containing pulverized monazite for about 3 months, psoriasis was eliminated. For the case in which the treated condition recurs after discontinuance of fitting such as in the present therapeutic example, fitting over a long period is necessary. However, for the long fitting, no side effects are expected for the patient as radiation is discontinuous and applied only while sleeping with very low dose irradiation. Furthermore, the therapeutic instrument for psoriasis according to the invention can be used repeatedly, which is very economical.

Therapeutic Example 2 (Psoriasis Therapeutic Example 2)

The patient was 41 year old male who was a free lancer. Crisis of common psoriasis had started from 29 years old on upper and lower limbs. Thereafter, psoriasis appeared on stretching sites and contracting sites of upper limbs and lower limbs, with much scale. No psoriasis appeared on the body trunk.

A therapeutic instrument according to the invention of the application similar to that prepared in the above-mentioned Example 1 in a form of a quilted bag (i.e., a thickness of about 10 mm, 170 cm×60 cm) containing pulverized monazite (from 60 to 70 mesh) was fitted near the entire part affected with psoriasis on the limbs and the back of the body for irradiation only while the patient slept. Although peeling of scales was decreased after 1 month, symptoms specific to psoriasis was not improved. After about 2 months, however, the stretching sites of both forearms were significantly improved. For example, the back part of hands were improved in such a way that any abnormality due to psoriasis could not be recognized immediately. And, after 3 months, it was improved to such an extent that a third person could not notice the lesion even though upper and lower limbs were exposed.

Therapeutic Example 3 (Cancer Recurrence Prevention Example 1)

The patient was a 66 year old male. Before he came to my clinic, he was subjected to an operation for gastric cancer (whole extraction of stomach). He came to my clinic on Feb. 2, 1994. During the operation for gastric cancer, cancer transfer to lymph nodes of the epigastrium which could not be excised was recognized after laparotomy, so that the operation was a non-radical operation. The doctor in charge notified only his family and not the patient that "cancer would progress and the patient would die within 1 year".

The therapy carried out in my clinic is to fit a therapeutic instrument according to the invention of the application similar to that prepared in the above-mentioned Example 1 in forms of quilted bags (the thickness of about 10 mm, 10 cm×10 cm) containing pulverized monazite (from 60 to 70 mesh) on epigastrium and the back thereof respectively. The fitting period was from 16 to 24 hours every day. Since there had been no observed progress of the cancer after 3 years of fitting, fitting was stopped. Furthermore, no radiation disorder due to fitting was apparent. Thereafter, transfer to the liver has not occurred at all which would be observed often without the benefit of fitting. About 4 years after the commencement of fitting, there is no observable abnormality due to cancer recurrence including subjective symptoms.

Therapeutic Example 4 (Cancer Recurrence Prevention Example 2)

The patient was 65 years old female. There was a shadow with a diameter of 2.5 cm in the central area of the right lung according to the diagnosis with the breast roentogenography at the clinic neighboring the patient on April, 1988. As a result of detailed examination in the clinic, her disease was diagnosed as lung cancer. However, the patient suffered from aortic insufficiency, so there was a danger of death if she was subjected to an operation for surgically excising a part of her lung. Further, the patient did not desire the excising operation.

The lesion was in the S6 area of the right lung, and transfer to the hilus pulmonis was not apparent.

She was fitted with a therapeutic instrument according to the invention of the application similar to that prepared is the above-mentioned Example 1 in a form of a quilted bag containing about 700 g of pulverized monazite (from 60 to 70 mesh), with a thickness of about 2 cm, on the S6 area of the right lung from May, 1988. Fitting was carried out continuously about 24 hours every day. The lesion (shadow) having the diameter of 2.5 cm was decreased to 1 cm 6 months after the commencement of fitting. After the fitting period had lapsed for about 2 years, the shadow of lesion became a string form, by which fibrosing was supposed by observation of the shadow. At that time (April, 1990), fitting of the above-mentioned circular therapeutic instrument was stopped. Thereafter, the patient has been well until March, 1998 for about 8 years.

Therapeutic Example 5 (Cancer Recurrence Prevention Example 3)

The patient was a 59 year old male. His disease was diagnosed as gastric cancer of Paulman type III by another clinic in May 1993 (5 years ago). He was recommended to be subjected to an operation, but he refused. He knew that the probability of death due to bad prognosis was not small even if the operation of gastric cancer was carried out.

His purpose of coming to my clinic was to investigate any method for extending his life as much as possible.

I explained as follows. That was, for the case of recommending the operation of a progressing cancer, my policy was to continue the low dose irradiation of radial rays on cancer cells to the patient at home after leaving the hospital as a post-operation treatment of gastric excision whether residual lesion (presence of cancer cells) was supposed or not.

The cancer part of about 6 cm was excised centering about the gastric angle. At the time of the operation, there was no transfer to the liver as observed with the naked eyes.

After the operation, a therapeutic instrument according to the invention of the application similar to that prepared in the above-mentioned Example 1 in a form of a quilted bag containing in a diameter of about 10 cm, about 700 g of pulverized monazite (from 60 to 70 mesh), with a thickness of about 2 cm, as the treatment for transfer to the liver and possible residual lesion at the epigastrium. The fitted sites were on the liver and back of the area below the sword projection. The fitting period was 2 years continuously; about 24 hours every day.

After the operation and fitting, the patient has engaged in general work without any complication recognized.

Therapeutic Example 6 (Atopic Dermatitis Therapeutic Example)

The patient was a 3 year old male child. He had papules during babyhood on his whole face, which were wetted to make crusts. He claimed a strong itching feeling and could not sleep well. His disease was diagnosed as atopic dermatitis by a neighboring doctor and was treated with an antihistaminic agent and cortical hormone, to come to a temporary lull. However, the affected area had gradually enlarged to include both the upper limbs and the body trunk gradually.

On Feb. 21, 1996 when he visited my clinic, there was a severe condition on the joint bending region, particularly the knee cavity. Since a diet therapy is important for atopic dermatitis, foods inducing allergic reactions (such as egg and soybeans) were avoided and gamma linoleic acid which is a precursor of prostaglandin $E_1$ ($PGE_1$) was administered. Since $PGE_1$ has anti-allergic action, the condition was improved gradually. However, the lesions on both lower legs remained. By applying a therapeutic instrument according to the invention of the application similar to that prepared in the above-mentioned Example 1 in a form of a quilted bag (containing about 200 g of pulverized monazite, having a thickness of 0.5 cm, a longitudinal size of 12 cm, and a transverse size of 5 cm), the condition was cured completely after 3 weeks. The reason why atopic dermatitis which had not been cured even with the above-mentioned PGE therapy for several months could be cured rapidly is supposed as an eminent effect of the therapy using this therapeutic instrument.

Therapeutic Example 7 (Articular Rhematism)

The patient was a 62 year old female. When she was examined in my clinic 10 years earlier, thermal feeling and articular expanded edema of both hand joints were recognized and edemas were also recognized widely on the back parts of her hands. In the index finger of metatarsal bone of the right foot, the distal end joint was deformed, and the index finger showed transition and deformation to the outside upper part.

She was subjected to a therapy for chronic articular rheumatism (RA) by an orthopedic surgeon, but the condition had progressed gradually to bring joint deformation and joint function disorder to various extents.

Although there are various therapeutic means for total steps of RA from a very initial step to a final step which brings physical handicap, this disease is naturally an autoimmune disease, so that an internal therapy is generally carried out before joint deformation.

As one means of treatment therefor, there is topical irradiation of low dose radioactivity. That is, the dose is from 80 to 100 kV for small joints and from 140 to 180 kV for large joints. The irradiated dose for one time is from 10 to 50 R (from 0.09 to 0.45 Sv (from 0.09 to 0.45 Gy)) for acute phase and from 70 to 100 R (from 0.63 to 0.91 Sv (from 0.63 to 0.91 Gy)) for the chronic phase. The irradiation times are from 5 to 10 for the cycle of once a week. However, instead of this, irradiation on the affected part by means of the therapeutic instrument according to the invention was carried out. For irradiation by means of a therapeutic instrument according to this invention, a therapeutic instrument in a form of a quilted bag (containing about 200 g of pulverized monazite (from 60 to 70 mesh), having a longitudinal size of 10 cm, a transverse size of 5 cm, and a thickness of about 1 cm) was fitted in contact with the affected parts (the back parts of both hands) every day while the patient slept for 7 to 8 hours. By continuing discontinuous irradiation for over 30 days, pain of the joints was relieved. Edema enlargement and thermal feeling of joints in both hands were decreased and the conditions were improved in many cases. Furthermore, edemas on the back parts of both hands which had not responded to conventional treatment easily disappeared and pain was relieved. It is considered that immune cells relating to articular rheumatism were expelled from infection sites by means of extremely low dose radioactivity. However, her joint function was not recovered. (For this case, it could not be recovered since the joints had been diseased for a long period and, thus, had been destroyed and deformed. For the case where joints are not destroyed, the recovery of functions can be expected.)

Industrial Applicability

Psoriasis, atopic dermatitis, articular rheumatism and/or cancer can be treated, or the condition or progress thereof can be prevented, or cancer cells can be made apoptosis, by applying near to the affected skin surface or to the nearest or near skin of the affected part, preferably within a range of from 0 to 50 mm, a radiation face of a therapeutic instrument composed of a solid radiation source having a half-life of within a range of from 20 to $1.41 \times 10^{10}$ years and a radioactivity corresponding to a decay rate within a range of from 10 to 370 Becquerel/g and a solid material coating the same, characterized in that the therapeutic instrument of the material has a radiation face for radiating radial rays emitted from the radiation source filtered by said solid material.

The effects obtained by the invention of the present application other than the above-mentioned ones will be mentioned as follows:

(1) A highly skilled technique is not necessary when using a radioactive substance with a very low level which, unlike high level radiation substances, is not regulated by laws for its handling.

(2) Strength of radioactivity is stable, since a radioactive substance having a long half-life is used.

(3) There is no danger of inhalation by air diffusion, since the radiation source is coated with solid material.

(4) It is simple, since only irradiation on the part contacted with or near to the affected part is necessary without any conventional low dose systemic irradiation on the whole body. Irradiation on the part which is highly sensitive to irradiation with radial rays can be avoided, or irradiation conditions can be selected.

(5) No erythema is apparent even after continuous irradiation for about 2 years. Therefore, therapy by means of the therapeutic instrument, according to this invention, can be carried out at home, so that patients may go to the hospital, for example, only once a month or once a half year for examination of the progress of the therapy.

(6) Therapy at home is possible by using the therapeutic instrument according to this invention, since therapy by means of conventional high dose X-ray irradiation or any therapy by means of low dose systemic irradiation is not necessary for the above-mentioned reasons. Furthermore, it is very economical.

(7) Since therapy by using the therapeutic instrument according to this invention is extremely safe, a high effect is expected for cases in which other therapeutic methods may be presumed to be difficult to carry out.

What is claimed is:

1. A method for treating or relieving psoriasis, the method comprises applying a radiation face of a therapeutic instrument over or on a skin surface affected with psoriasis, wherein the therapeutic instrument is composed of a solid radiation source and a solid material sealing or enveloping the same, in which the solid material has the radiation face for radiating radial rays emitted from the solid radiation source, the solid radiation source has a half-life ranging from 20 to $1.41 \times 10^{10}$ years and a radioactivity corresponding to a decay rate ranging from 10 to 370 Becquerel/g, and a strength of the radial rays emitted from a center part of the radiation face is from 10 to 100 $\mu$Sv/hr.

2. A method according to claim 1, wherein a distance between the radiation face and the skin surface affected with psoriasis is from 0 to 50 mm.

3. A method according to claim 2, wherein the solid radiation source is a radioactive element of $^{232}$Th or a radioactive decay series in which the element is a parent.

4. A method according to claim 3, wherein the solid material is a vessel composed of a soft and flexible textile, nonwoven fabric or membrane, and inner surface thereof is quilted in order that powders of the solid radiation source are not unevenly distributed.

5. A method according to claim 2, wherein the solid radiation source is monazite.

6. A method according to claim 2, wherein the solid material is a vessel composed of a soft and flexible textile, nonwoven fabric or membrane, and inner surface thereof is quilted in order that powders of the solid radiation source are not unevenly distributed.

7. A method according to claim 1, wherein the solid radiation source is a radioactive element of $^{232}$Th or a radioactive decay series in which the element is a parent.

8. A method according to claim 7, wherein the solid material is a vessel composed of a soft and flexible textile, nonwoven fabric or membrane, and inner surface thereof is quilted in order that powders of the solid radiation source are not unevenly distributed.

9. A method according to claim 1, wherein the solid radiation source is monazite.

10. A method according to claim 9, wherein the solid material is a vessel composed of a soft and flexible textile, nonwoven fabric or membrane, and inner surface thereof is quilted in order that powders of the solid radiation source are not unevenly distributed.

11. A method according to claim 1, wherein the solid material is a vessel composed of a soft and flexible textile, nonwoven fabric or membrane, and inner surface thereof is quilted in order that powders of the solid radiation source are not unevenly distributed.

12. A method for treating or relieving a disease selected from the group consisting of atopic dermatitis, articular rheumatism and cancer, the method comprises applying a radiation face of a therapeutic instrument over or on a skin surface affected with atopic dermatitis or skin cancer, or over or on the skin surface near or nearest to a part affected with articular rheumatism or cancer, or over or on a part affected with cancer, wherein the therapeutic instrument is composed of a solid radiation source and a solid material sealing or enveloping the same, in which the solid material has the radiation face for radiating radial rays emitted from the solid radiation source, the solid radiation source has a half-life ranging from 20 to $1.41 \times 10^{10}$ years and a radioactivity corresponding to a decay rate ranging from 10 to 370 Becquerel/g, and strength of the radial rays emitted from center part of the radiation face is from 10 to 100 $\mu$Sv/hr.

13. A method according to claim 12, wherein a distance between the radiation face and the skin surface affected with atopic dermatitis or skin cancer, or a distance between the radiation face and the skin surface near or nearest to a part affected with articular rheumatism or cancer is from 0 to 50 mm.

14. A method according to claim 13, wherein the solid radiation source is a radioactive element of $^{232}$Th or a radioactive decay series in which the element is a parent.

15. A method according to claim 14, wherein the solid material is a vessel composed of a soft and flexible textile, nonwoven fabric or membrane, and inner surface thereof is quilted in order that powders of the solid radiation source are not unevenly distributed.

16. A method according to claim 13, wherein the solid radiation source is monazite.

17. A method according to claim 13, wherein the solid material is a vessel composed of a soft and flexible textile, nonwoven fabric or membrane, and inner surface thereof is quilted in order that powders of the solid radiation source are not unevenly distributed.

18. A method according to claim 12, wherein the solid radiation source is a radioactive element of $^{232}$Th or a radioactive decay series in which the element is a parent.

19. A method according to claim 18, wherein the solid material is a vessel composed of a soft and flexible textile, nonwoven fabric or membrane, and inner surface thereof is quilted in order that powders of the solid radiation source are not unevenly distributed.

20. A method according to claim 12, wherein the solid radiation source is monazite.

21. A method according to claim 20, wherein the solid material is a vessel composed of s soft and flexible textile, nonwoven fabric or membrane, and inner surface thereof is quilted in order that powders of the solid radiation source are not unevenly distributed.

22. A method according to claim 12, wherein the solid material is a vessel composed of a soft and flexible textile, nonwoven fabric or membrane, and inner surface thereof is quilted in order that powders of the solid radiation source are not unevenly distributed.

* * * * *